US012734184B2

(12) United States Patent
Ivarsson

(10) Patent No.: US 12,734,184 B2
(45) Date of Patent: Sep. 15, 2026

(54) CLINICAL DOSING SCHEDULE OF INOSITOL PHOSPHATE OLIGO(ETHYLENE GLYCOL) COMPOUNDS

(71) Applicant: VIFOR (INTERNATIONAL) AG, St. Gallen (CH)

(72) Inventor: Mattias Emanuel Ivarsson, Zürich (CH)

(73) Assignee: VIFOR (INTERNATIONAL) AG, St. Gallen (CH)

( * ) Notice: Subject to any disclaimer, the term of this patent is extended or adjusted under 35 U.S.C. 154(b) by 350 days.

(21) Appl. No.: 18/262,591

(22) PCT Filed: Jan. 26, 2022

(86) PCT No.: PCT/EP2022/051694

§ 371 (c)(1),
(2) Date: Jul. 24, 2023

(87) PCT Pub. No.: WO2022/161980

PCT Pub. Date: Aug. 4, 2022

(65) Prior Publication Data

US 2024/0100074 A1 Mar. 28, 2024

(30) Foreign Application Priority Data

Jan. 26, 2021 (EP) .................................... 21153605

(51) Int. Cl.
*A61K 31/6615* (2006.01)
*A61K 9/00* (2006.01)
*A61P 39/00* (2006.01)

(52) U.S. Cl.
CPC ........ *A61K 31/6615* (2013.01); *A61K 9/0004* (2013.01); *A61P 39/00* (2018.01)

(58) Field of Classification Search
CPC ....... A61K 31/6615; A61K 47/02; A61P 9/10; A61P 9/14; A61P 39/00; A61P 43/00
See application file for complete search history.

(56) References Cited

U.S. PATENT DOCUMENTS

2014/0271915 A1* 9/2014 Perello Bestard ..... A61K 31/59 514/141
2020/0179422 A1 6/2020 Perello Bestard

FOREIGN PATENT DOCUMENTS

WO 2017098047 6/2017

OTHER PUBLICATIONS

Khan et. al., Nat. Rev. Dis. Primers, vol. 2, pp. 1-50, publ. Nov. 2017 (Year: 2017).*

Makoto Kuro-o, "Molecular Mechanisms Underlying Accelerated Aging by Defects in the FGF23-Klotho System," Hindawi International Journal of Nephrology, vol. 2018, Article ID 967984, pp. 1-6, Published: May 21, 2018 (May 21, 2018).

Schantl Antonia E. et al, "Inhibition of vascular calcification by inositol phosphates derivatized with ethylene glycol oligomers", Nature Communications, vol. 11, No. 1, Feb. 5, 2020, p. 721.

Schantl Antonia E. et al, "Investigational Pharmacological Treatments for Vascular Calcification", Advanced Therapeutics, vol. 2, No. 1, Sep. 30, 2018, p. 1800094.

Wu Meiting et al, "Vascular Calcification: An Update on Mechanisms and Challenges in Treatment", Calcified Tissue International, vol. 93, No. 4, Mar. 1, 2013, p. 365-373.

Jacobs Ida Joely et al., "A phytic acid analogue INS-3001 prevents ectopic calcification in an Abcc6 −/− mouse model of pseudoxanthoma elasticum", Experimental Dermatology,vol. 30, No. 6, Feb. 1, 2021 (Feb. 1, 2021), p. 853-858.

Record History, NCT04195906, ver 11, Nov, 9, 2020, clinicaltrials.gov, National Library of Medicine.

Ferrer et al., "SNF472 Is More Efficacious In Vivo Than Its 4,6-bisPEGylated Derivative in Inhibiting Vascular Calcification in Rats", Journal of the American Society of Nephrology, 2019, vol. 30, p. 210 TH-PO367 (Year: 2019).

* cited by examiner

*Primary Examiner* — Sarah Pihonak
(74) *Attorney, Agent, or Firm* — JMB Davis Ben-David

(57) ABSTRACT

The invention relates to a dosing schedule for an inositol polyphosphate oligo(ethylene glycol) compound, or its pharmaceutically acceptable salt used in the treatment or prevention of a disease associated with formation of, and/or tissue exposure to, calcium salt crystals. The drug compound is administered at an interval of one week.

8 Claims, 3 Drawing Sheets

(A)
Control
untreated
pump
0.16 mg/kg/day
pump
0.8 mg/kg/day
pump
4 mg/kg/day
s.c. 0.8 mg/kg/day
once weekly
s.c. 4 mg/kg/day
once weekly
s.c. 14 mg/kg/day
once weekly
s.c. 4 mg/kg/day
Thrice weekly
(B)
Control
untreated
pump
4 mg/kg/day

| Genotype | WT | Abcc6-/- | Abcc6-/- | Abcc6-/- | Abcc6-/- | Abcc6-/- | Abcc6-/- | Abcc6-/- | Abcc6-/- | Abcc6-/- | Abcc6-/- | Abcc6-/- | Abcc6-/- |
|---|---|---|---|---|---|---|---|---|---|---|---|---|---|
| mg/kg/day | | | 0.16 | 0.8 | 4 | 20 | 100 | 0.8 | 4 | 14 | 4 | | 4 |
| Delivery | | | pump | pump | pump | pump | pump | s.c., 1/week | s.c., 1/week | s.c., 1/week | s.c., 3/week | | pump |
| | Prevention study | | | | | | | | | | | Established disease study | |

CLINICAL DOSING SCHEDULE OF INOSITOL PHOSPHATE OLIGO(ETHYLENE GLYCOL) COMPOUNDS

CROSS-REFERENCE TO RELATED APPLICATION

This is the U.S. National Stage of International Patent Application No. PCT/EP2022/051694 filed on Jan. 26, 2022, which claims priority to European Patent Application Ser. No. 21/153,605.7 filed on Jan. 26, 2021.

The present invention relates to compounds and compositions for use in treatment of conditions associated with calcification of tissue, particularly cardiovascular tissue, caused by deposition of, or exposure to, calcium phosphate (CaP) and other calcium precipitates.

This application claims priority of European application EP21153605, filed 26 Jan. 2021, and incorporated by reference herein in its entirety.

BACKGROUND OF THE INVENTION

WO2013045107 (A1) first discloses the concept of using inositol polyphosphate oligo(ethylene glycol) derivatives as pharmaceutical agents. Initially conceived as an agent of considerable potential to neutralize *C. difficile* toxin in the colon lumen, subsequent analysis found that the compounds are highly effective in reducing calcification when applied systemically, as first disclosed in WO2017098047 (A1), U.S. Pat. No. 10,624,909 (B2) and US20200247837 (A1).

All patent documents mentioned in the present specification are incorporated herein by reference in their entirety.

The inventors investigated the pharmacological profile of inositol phosphate oligo(ethylene glycol) derivatives in several studies and found that the compounds did not accumulate following repeated daily administrations over a course of seven days (see Schantl et al., Nature Communications 11, 721 (2020); https://doi.org/10.1038/s41467-019-14091-4).

The objective of the present invention is to provide advantageous dosing schedules of inositol polyphosphate oligo(ethylene glycol) derivatives. This objective is attained by the subject-matter of the independent claims of the present specification.

SUMMARY OF THE INVENTION

The invention relates to a dosing schedule of an inositol polyphosphate oligo(ethylene glycol) compound, or its pharmaceutically acceptable salt, for use in treatment or prevention of a disease associated with formation of, and/or tissue exposure to, calcium salt crystals. According to the invention, the inositol polyphosphate oligo(ethylene glycol) compound is administered at weekly intervals or longer spaced intervals.

Terms and Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

The terms "comprising," "having," "containing," and "including," and other similar forms, and grammatical equivalents thereof, as used herein, are intended to be equivalent in meaning and to be open ended in that an item or items following any one of these words is not meant to be an exhaustive listing of such item or items, or meant to be limited to only the listed item or items. For example, an article "comprising" components A, B, and C can consist of (i.e., contain only) components A, B, and C, or can contain not only components A, B, and C but also one or more other components. As such, it is intended and understood that "comprises" and similar forms thereof, and grammatical equivalents thereof, include disclosure of embodiments of "consisting essentially of" or "consisting of."

Where a range of values is provided, it is understood that each intervening value, to the tenth of the unit of the lower limit, unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

Reference to "about" a value or parameter herein includes (and describes) variations that are directed to that value or parameter per se. For example, description referring to "about X" includes description of "X."

As used herein, including in the appended claims, the singular forms "a," "or," and "the" include plural referents unless the context clearly dictates otherwise.

In the context of the present specification, the term oligo(ethylene glycol) relates to oligomers of ethylene glycol and close chemical relatives such as oligo-propylene glycol and oligo-glycerol. The term "oligo" signifies that more than one, particularly from 2 to 20, more particularly from 2 to 12 monomers ($—CH_2—CH_2—O—$) are present.

The term calcification in the context of the present specification relates to the formation of calcium precipitates in the affected tissue, particularly renal tissue or the cardiovascular system.

The term "an interval of one week" when applied to administration of a compound means that the compound is administered to a patient at day one of a dosing schedule, and then on day eight, but not on the intervening days.

DETAILED DESCRIPTION OF THE INVENTION

A first aspect of the invention relates to an inositol polyphosphate oligo(ethylene glycol) compound, or its pharmaceutically acceptable salt, for use in treatment or prevention of a disease associated with formation of, and/or tissue exposure to, calcium salt crystals, wherein the inositol polyphosphate oligo(ethylene glycol) drug compound is administered at an interval of one week, or at longer intervals exceeding one week.

In the broadest sense, the disease for which the weekly dosing schedule is provided, is kidney or cardiovascular disease associated with calcium salt precipitation, particularly with the formation of precipitates comprised of calcium phosphate and/or oxalate.

In certain embodiments, the inositol polyphosphate oligo (ethylene glycol) compound, or its pharmaceutically acceptable salt, for use according to the invention by weekly administration, is described by a general formula I (I)

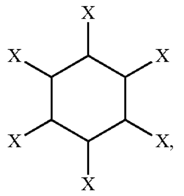

wherein one or two or three X are oligo(ethylene glycol) and the remaining X are $OPO_3^{2-}$.

In certain particular embodiments, the inositol polyphosphate oligo(ethylene glycol) compound, or its pharmaceutically acceptable salt is described by formula I wherein two X are oligo(ethylene glycol) and the remaining four X are $OPO_3^{2-}$. This encompasses the bis-oligoethylene myo-inositol tetrakisphosphate compound shown below as formula (I a), which is the compound used in the examples.

In certain particular embodiments, the inositol polyphosphate oligo(ethylene glycol) compound, or its pharmaceutically acceptable salt, for use according to the invention by weekly administration, is described by formula I wherein three X are oligo(ethylene glycol) and the remaining three X are $OPO_3^{2-}$. The inventors have shown previously that the tris-oligoethylene myo-inositol trisphosphate compounds have an efficacy in preventing calcium salt precipitation that is comparable to the bis-OEG compounds.

In certain particular embodiments, the inositol polyphosphate oligo(ethylene glycol) compound, or its pharmaceutically acceptable salt, for use according to the invention by weekly administration, is described by formula I wherein one X is oligo(ethylene glycol) and the remaining five X are $OPO_3^{2-}$.

In certain particular embodiments, the inositol polyphosphate oligo(ethylene glycol) compound, or its pharmaceutically acceptable salt, for use according to the invention by weekly administration, is described by formula I wherein the oligo(ethylene glycol) is described by a formula $O—(CH_2—CH_2—O)_nCH_3$, with n being selected from an integer between 2 and 20, particularly n being 2 to 12.

In certain more particular embodiments, the inositol polyphosphate oligo(ethylene glycol) compound, or its pharmaceutically acceptable salt, for use according to the invention by weekly administration, is described by formula I wherein the oligo(ethylene glycol) is described by a formula $O—(CH_2—CH_2—O)_nCH_3$, wherein n is 2.

In certain very particular embodiments, the inositol polyphosphate oligo(ethylene glycol) compound, or its pharmaceutically acceptable salt is described by formula I a:

(I a)

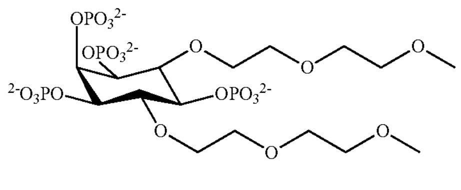

In other particular embodiments, the inositol polyphosphate oligo(ethylene glycol) compound, or its pharmaceutically acceptable salt is described by formula I b:

(I b)

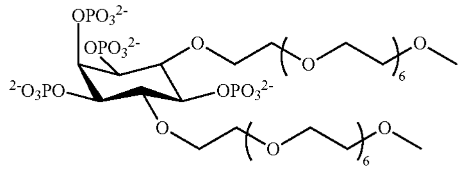

In other particular embodiments, the inositol polyphosphate oligo(ethylene glycol) compound, or its pharmaceutically acceptable salt is described by formula I c:

(I c)

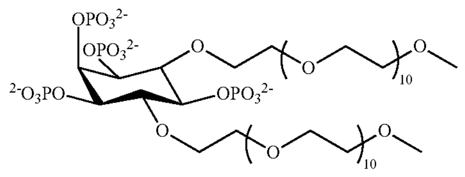

In other particular embodiments, the inositol polyphosphate oligo(ethylene glycol) compound, or its pharmaceutically acceptable salt is described by formula I d:

(I-d)

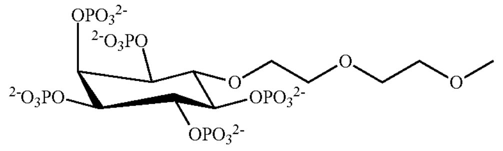

In other particular embodiments, the inositol polyphosphate oligo(ethylene glycol) compound, or its pharmaceutically acceptable salt is described by formula I e:

(I-e)

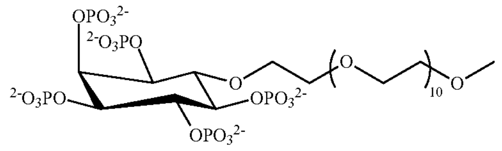

In certain embodiments, the compound is administered to a human patient at a dose of between 60 nmol/kg/day to 1700 nmol/kg/day.

The inventors have calculated this dose based on the observed profile (see Examples and Figures) of compound I a, which was effective in a range of approximately 0.5 mg/kg/day to 15 mg(kg*day)$^{-1}$ in a mouse model. Using the well know conversion figure (see: Guidance for Industry; Estimating the Maximum Safe Starting Dose in Initial Clinical Trials for Therapeutics in Adult Healthy Volunteers; U.S. Department of Health and Human Services Food and Drug Administration, Center for Drug Evaluation and Research (CDER), July 2005), the conversion factor for converting mouse to human dosing schedules is 0.08, yielding a range of 40 to 1200 μg/kg/day. Using the molecular mass of (I a) of 698 g/mol (which does not count the counterion into the weight), this yields the above range.

In particular embodiments, an inositol polyphosphate oligo(ethylene glycol) compound is delivered weekly at a dose of between 90 nmol/kg/day to 1600 nmol/kg/day, equivalent to a dose of 65 μg/kg/day to 1100 μg/kg/day in a human subject, or 0.8 mg/kg/day and 14 mg/kg/day in the mouse model.

In other particular embodiments, an inositol polyphosphate oligo(ethylene glycol) compound is delivered weekly at a dose of between 170 nmol/kg/day to 2500 nmol/kg/day, equivalent to a dose of 120 μg/kg/day to 1750 μg/kg/day in a human subject.

In more particularly embodiments, an inositol polyphosphate oligo(ethylene glycol) compound is delivered weekly at a dose of between 170 nmol/kg/day to 600 nmol/kg/day, equivalent to 120 to 400 μg/kg/day of compound (I a), 1.5 to 5 mg/kg/day in the mouse model.

In certain embodiments, the inositol polyphosphate oligo (ethylene glycol) compound, or its pharmaceutically acceptable salt, is administered for use according to the invention, at a dose to sustain a plasma level exceeding 10 ng/mL, particularly at a dose sustaining a plasma level of 10 ng/mL to 50 μg/mL, more particularly at a dose sustaining a plasma level of 100 ng/mL to 5 μg/mL.

In the examples, the inositol polyphosphate oligo(ethylene glycol) compound was administered for weekly administration as a solution at a concentration of approximately 0.1 mL/10 g bodyweight (10 ml/kg) in accordance to standard practices. The solution is adjusted to neutral or slightly acidic pH in the range of pH 6 to 7.5. In the examples presented herein, a sodium salt was used.

Calcium Precipitates

The chemical composition of calcium crystalline precipitates associated with renal and cardiovascular disease is well studied (see Elliot, J Urology 100 (1968), 687-693; Xie et al., Cryst Growth Des. 2015 Jan. 7; 15(1): 204-211). In principle, the treatment according to the invention is capable of preventing or ameliorating any condition in which deposition of calcium phosphate, oxalate and mixed calcium phosphate-oxalate crystals play a role.

Calcium phosphate is found in different crystal forms in pathologic deposits in the human body; these include hydroxyapatite (hydroxylapatite, HA, $Ca_{10}(PO_4)_6(OH)_2$), brushite ($CaHPO_4$*2 $H_2O$), monetite, and various amorphous calcium phosphate salts.

Calcium oxalate in pure form is found as a mono-(whewellite), di-(weddellite) and tri-hydrate, and often associated with other deposits, mainly phosphate salts.

The results presented in the examples were obtained with a murine model of pseudoxanthoma elasticum (PXE), a prototype of heritable ectopic calcification disorders.

PXE affects the skin, eyes, and the cardiovascular system due to inactivating mutations in the ABCC6 gene. In the examples shown below, the inventors demonstrate the efficacy of the inositol polyphosphate oligo(ethylene glycol) compound (I a) in inhibiting ectopic calcification in an Abcc6−/− mouse model of PXE.

In a prevention study, Abcc6−/− mice, at 6 weeks of age, the time of onset of ectopic calcification, were treated with the compound with 0.16, 0.8, 4, 20 or 100 mg/kg/day administered by subcutaneous implantation of osmotic pumps, as well as 4 mg/kg/day administered by subcutaneous injection thrice weekly or 14, 4, and 0.8 mg/kg/day by once weekly subcutaneous injection. Mice were necropsied at 12 weeks of age. Histologic examination and quantitative calcium assay revealed that mice receiving 6 weeks of continuous drug administration via osmotic pumps showed dose-dependent inhibition of muzzle skin calcification with complete response at 4 mg/kg/day and a minimum effective dose at 0.8 mg/kg/day. The drug compound's plasma concentrations were dose-dependent and largely consistent during treatment for each dose. Thrice weekly and once weekly subcutaneous injections of (I a) also prevented calcification. In a treatment study, 12-week-old Abcc6−/− mice with evident calcification were continuously administered INS-3001 at 4 mg/kg/day for a follow-up of 12 weeks. Treatment according to the invention was found to stabilize existing calcification that had developed at the start of treatment. These results demonstrate that the compounds and schedule according to the invention provides a promising approach to treating any ectopic calcification disorder.

The results presented herein facilitate the use of the weekly treatment schedule for a number of diseases:

Diseases Associated to Calcium Precipitation that Benefit from Treatment According to the Invention "Renal fibrosis" or "tubulointerstitial fibrosis" associated with formation of, and/or tissue exposure to, calcium salt crystals, refers to a thickening and scarring of kidney tissue, due to unsuccessful wound-healing after chronic injury due to exposure to calcium phosphate, calcium oxalate or mixed CaP/CaOx precipitates. During this process fibrotic matrix deposition continues unchecked leading to glomerulosclerosis, tubular atrophy and interstitial fibrosis. Patients suffering from said disease can experience intense abdominal pain (with bleeding or haemorrhaging), swelling and discoloration in one or both legs, and ultimately progress to chronic kidney disease.

"Renal inflammation" or "nephritis" is defined as a complex network of interactions between renal parenchymal cells and resident immune cells, such as macrophages and dendritic cells, coupled with recruitment of circulating monocytes, lymphocytes, and neutrophils. Once stimulated, these cells activate specialized structures such as Toll-like receptor and Nod-like receptor (NLR). By detecting danger-associated molecules, these receptors can set in motion major innate immunity pathways such as nuclear factor κB (NF-κB) and NLRP3 inflammasome, causing metabolic reprogramming and phenotype changes of immune and parenchymal cells and triggering the secretion of a number of inflammatory mediators that can cause irreversible tissue damage and functional loss. In CKD, a chronic inflammation leads to a progressively decreasing glomerular filtration rate (GFR) that can ultimately result in kidney failure (end stage renal disease, ESRD).

To the extent that renal inflammation/nephritis is associated or caused by interaction of renal tissue with calcium deposits, the treatment according to the invention is expected to ameliorate or prevent the condition. The examples shown herein demonstrate that calcium phosphate deposition/exposure leads to upregulation of inflammation and fibrosis markers in the kidneys, therefore any disease that consists of inflammation and fibrosis of the kidneys should benefit from treatment that inhibits the formation of deposits. For each of these inflammatory conditions, there may also be other, even concurrent causes for the inflammation and fibrosis, as both of these are often multifactorial processes. Abrogation of one contributing factor, however, is expected to improve the overall clinical picture.

"Glomerulonephritis" refers to a group of diseases that are characterized by inflammatory changes in glomerular capillaries. Patients suffering from said group of diseases can experience proteinuria, impaired renal function in some cases paired with fluid retention, hypertension and oedema.

Glomerulonephritis can occur as a primarily renal disease as well as indicate a systematic disease process. When associated with formation of, and/or tissue exposure to, calcium salt crystals, glomerulonephritis is expected to benefit from treatment with the compounds described herein.

"Interstitial nephritis" refers to inflammation of the renal interstitium which can be caused by unbalanced levels of calcium. Symptoms include increased urine output, hematuria, changes in mental status, swelling. This condition, if associated associated with formation of, and/or tissue exposure to, calcium salt crystals, is expected to benefit from treatment with the compounds described herein.

"Phosphate-induced renal fibrosis" may be associated with a range of calcium and phosphate concentrations that lead to precipitation in the renal tubules, see the data presented in FIG. 2: i.e. calcium >2 or 5 mmol/L and phosphate >5 or 7 mmol/L. Of note, there can be elevated phosphate in renal tubular fluid (leading to its precipitation with calcium) even when detectable plasma phosphate levels are normal (i.e. in the absence of hyperphosphatemia). Elevated plasma phosphate is a terminal consequence of end-stage renal disease that occurs when kidney function is below a 20% threshold.

"Phosphate-induced chronic kidney disease" Phosphate-induced CKD can occur even if plasma phosphate levels are normal (i.e. in earlier stage CKD patients). Reference values can be calcium >2 or 5 mmol/L and phosphate >5 or 7 mmol/L in the renal tubules.

"Chronic kidney disease associated with hyperphosphatemia" refers to hyperphosphatemia occurring in progressive CKD, due to the increasing loss of GFR. This leads to the blocking of tubular phosphate reabsorption and therefore increased phosphate retention, in other words, less phosphate clearance, impairing phosphate homeostasis (Sharon M. Moe, Prim Care. 2008 June; 35(2): 215—vi.). A useful reference value to characterize patients who are expected to benefit from the treatment according to the invention can be a plasma phosphate level of >1.46 mmol/Ls.

"Progression of chronic kidney disease" refers to five stages, ranging from the first stage (mild damage, eGFR 90 or greater) to the fifth (complete kidney failure, eGFR less than 15). Current guidelines determine the critical GFR for CKD to be less than 60 mL/min per 1.73 $m^2$ over a period of 3 months.

"Phosphate toxicity" refers to a dysregulated renal phosphate excretion and reabsorption, impairing phosphate homeostasis, which can cause severe damage of kidney tissue. (Razzaque, Clin Sci (Lond). 2011 February; 120(3): 91-97). To the extent that this condition causes tissue damage associated with formation of, and/or tissue exposure to and/or deposition of crystals which can avoided by the treatment according to the invention, the treatment is indicated for patient suffering from the condition.

"Hyperphosphaturia" or "phosphaturia" refers to a high level of phosphate in urine. To the extent that this condition causes tissue damage associated with formation of, and/or tissue exposure to and/or deposition of crystals which can avoided by the treatment according to the invention, the treatment is indicated for patient suffering from the condition.

"Hyperphosphatemia" refers to an elevated (>4.5 mg/dL; >1.46 mmol/L) phosphate level in blood. To the extent that this condition causes tissue damage associated with formation of, and/or tissue exposure to and deposition of crystals which can avoided by the treatment according to the invention, the treatment is indicated for patient suffering from the condition.

"Hyper-FGF23-emia" refers to an increased fractional phosphate excretion, paired with a decrease of serum phosphate levels, due to elevated fibroblast growth factor (FGF)-23 levels.

"Vascular calcification" refers to the pathological deposition of minerals in the vascular system often observed in patients suffering from CDK or diabetes. The elevated calcium and/or phosphate levels can be the result of metabolic dysregulation caused by diabetes, dyslipidemia, oxidative stress, uremia, and hyperphosphatemia, which lead to osteoblast-like cell formation, appearance of calcified deposits and stiffening in the vessel wall.

"Coronary artery disease" or "artheroslerotic heart disease" refers to an accumulation of plaque in damaged inner layers of the coronary artery. Factors such as inflammatory cells, lipoproteins and calcium attach to the plaque leading to further stenosis. Progression of this disease can ultimately lead to myocardial infarction or stroke.

"Vascular stiffening" refers to stiffening of the arterial wall due to calcification. Vascular stiffening consists of lower elasticity of the vasculature leading to an increased pulse wave pressure.

"Valve calcification", particularly aortic valve calcification, refers to an active dysregulation of normal homeostatic processes and hemodynamic changes, such as ECM degradation, fibrosis, lipid accumulation, and neo-angiogenesis of the valve tissue, concurrent with calcification of the valve, in particular the aortic and mitral valves.

"Nephrocalcinosis" refers to the deposition of calcium salts in the renal parenchyma, particularly in the medulla (medullary nephrocalcinosis) or cortex (cortical nephrocalcinosis) of the kidney.

"Calcinosis cutis" refers to the deposition of calcium phosphate precipitates within the skin, particularly within the extremities. If the solubility point of calcium and phosphate are exceeded, precipitation of calcium salts and deposition as amorphous hydroxyapatite occur.

"Kidney stones", "renal calculi", "nephrolithiasis", and "urolithiasis" refer to a mineral deposit in renal tissue, which is due to the accumulation and therefore supersaturation of urine (hypercalcuria).

"Chondrocalcinosis" refers to the accumulation of calcium phosphate in joints.

Particular conditions the treatment of which is expected to benefit, based on the examples described in here, from administration of the compounds described in here further include aortic valve stenosis, peripheral artery disease and brain calcification.

In certain embodiments, the diseases associated with calcification addressed by the weekly dosing regimen according to the invention include: myocardial infarction, cardiovascular mortality, progression of chronic kidney disease, peripheral arterial disease, critical limb ischemia, calciphylaxis, general arterial calcification of infancy, aortic stenosis, atherosclerosis, pseudoxanthoma elasticum, cardiac hypertrophy, heart failure, arrhythmia, aneurysm, valvular stenosis, aortic regurgitation, mitral stenosis, mitral regurgitation, stroke, and decline of cognitive function, each being associated with deposits of calcium salts in the affected tissue.

The data shown in example 1 confirm the utility of the compounds disclosed herein as effective in reducing or inhibiting calcium phosphate crystal formation, in the prevention and treatment of idiopathic calcium nephrolithiasis/ idiopathic calcium kidney stones, particularly those mainly consisting of calcium phosphate, calcium oxalate, or mixtures thereof.

In certain embodiments, the inositol polyphosphate oligo (ethylene glycol) compound, or its pharmaceutically acceptable salt, for use in treatment or prevention of the diseases laid out above, is described by a general formula I, wherein one or two or three X are oligo(ethylene glycol) and the remaining X are $OPO_3^{2-}$.

(I)

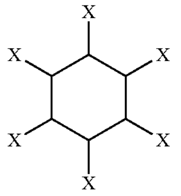

When dissolved in aqueous medium at physiological pH, it is apparent to the skilled artisan that the compounds mentioned herein are anionic and will be accompanied by cations.

In certain particular embodiments, two of the inositol substituents X shown in the above formula I are oligo (ethylene glycol) and the remaining four X are $OPO_3^{2-}$.

Examples for compounds that can be advantageously used in treatment according to the invention include general formulas I-1, I-2, I-3 and I-4, wherein in each case, X is phosphate and $R^1$ is an oligo(ethylene glycol) as set forth herein:

(I-1)

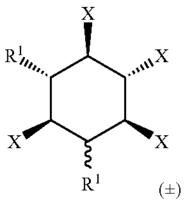

(±)

(I-2)

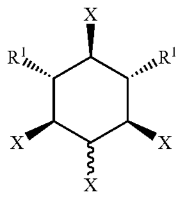

(I-3)

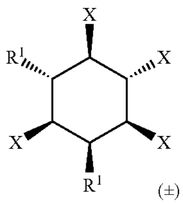

(±)

-continued (I-4)

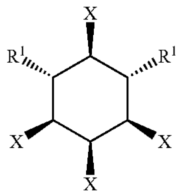

In one more particular embodiment thereof, the scaffold is myo-inositol and the oligo(ethylene glycol) substituents are on position 4 and 6, with the rest of the substituents being phosphate. In an even more particular embodiment, the oligo(ethylene glycol) substituents are $O—(CH_2—CH_2O)_2—CH_3$.

In other particular embodiments, one of the inositol substituents X shown in the above formula I is oligo (ethylene glycol) and the remaining five X are $OPO_3^{2-}$. In one more particular embodiment thereof, the scaffold is myo-inositol and the oligo(ethylene glycol) substituent is on position 4 or 6, particularly on 6, with the rest of the substituents being phosphate. In an even more particular embodiment, the oligo(ethylene glycol) substituent is $O—(CH_2—CH_2O)_2—CH_3$.

In yet other particular embodiments, three of the inositol substituents X shown in the above formula I are oligo (ethylene glycol) and the remaining three X are $OPO_3^{2-}$. Examples thereof include general formulas I-5 and I-6, wherein in each case, X is phosphate and $R^1$ is an oligo (ethylene glycol) as set forth herein:

(I-5)

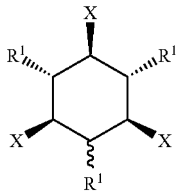

(I-6)

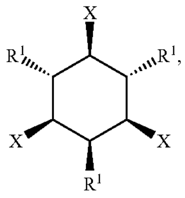

In certain embodiments, the oligo(ethylene glycol) substituent (or substituents) of the inositol polyphosphate oligo (ethylene glycol) compound, or its pharmaceutically acceptable salt, provided for use according to the invention herein, is described by a formula $O—(CH_2—CH_2—O)_nCH_3$, with n being selected from an integer between 2 and 20, particularly n being 2 to 12. Different parameters of the compounds' physiological activity, pharmacological parameters and aspects of manufacture will influence which value of n is optimal.

In certain particular embodiments, the oligo(ethylene glycol) substituent (or substituents) of the inositol polyphosphate oligo(ethylene glycol) compound, or its pharmaceutically acceptable salt, provided for use according to the invention herein, is described by a formula $O—(CH_2—$ $CH_2$—$O)_nCH_3$, wherein n is 2. The examples demonstrate the particular advantage of $(OEG_2)_2$—IP4 (Ia), wherein n is 2.

Certain particular embodiments of the compound for use as specified herein are described by any one of the formulas:

(I a)

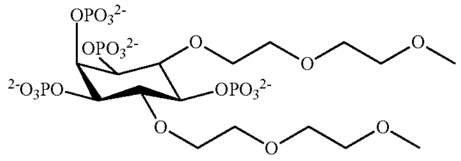

(I b)

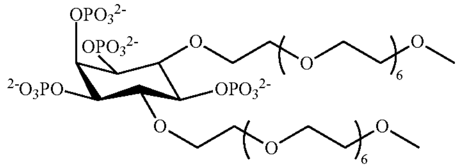

(I c)

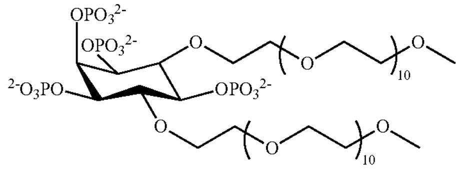

Certain particular embodiments of the compound for use as specified herein are described by any one of the formulas:

(I d)

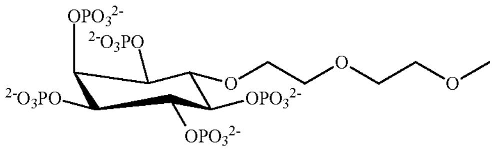

(I e)

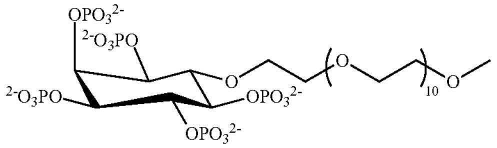

Other embodiments of compounds for use according to aspect of the invention include:

(I f)

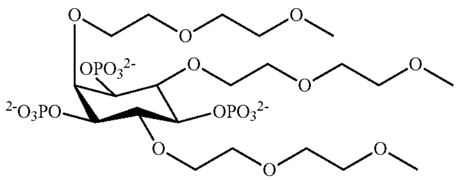

-continued (I g)

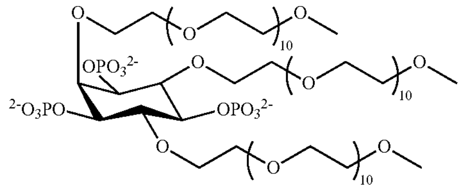

Any of the inositol polyphosphate oligo-alkyl ether compounds, or their pharmaceutically acceptable salt, are provided for use in treatment or prevention of a disease associated with the formation of calcium phosphate salt or other solid precipitate in the body, particularly in renal tissue.

The administration of compounds having two oligo(ethylene glycol) moieties attached to a myo-inositol tetrakisphosphate scaffold (I a) is of particular advantage in treatment or prevention of diseases as set forth herein that are associated with precipitation of calcium phosphate solid matter, and in prevention or treatment of mixed phosphate-oxalate calcium precipitates, or precipitates that mainly contain oxalate but originate from calcium phosphate nuclei, as evidenced by the data provided in example 1 and as exemplified by the growth of calcium oxalate kidney stones on calcium phosphate-based Randall's plaque.

The bipegylated compounds such as $(OEG2)_2$—IP4 also have a protective effect in the context of mixed precipitates (CaP+CaOx).

The skilled person is aware that any specifically mentioned drug compound mentioned herein may be present as a pharmaceutically acceptable salt of said drug. Pharmaceutically acceptable salts comprise the ionized drug and an oppositely charged counterion. Non-limiting examples of pharmaceutically acceptable cationic salt forms include aluminium, benzathine, calcium, ethylene diamine, lysine, magnesium, meglumine, potassium, procaine, sodium, tromethamine and zinc.

Method of Manufacture and Method of Treatment According to the Invention

The invention further encompasses, as an additional aspect, the use of an inositol polyphosphate oligo(ethylene glycol) compound, or its pharmaceutically acceptable salt, as specified in detail above, for use in a method of manufacture of a medicament for the treatment or prevention of a disease associated with formation of calcium salt precipitate or calcium salt crystals, specifically in a disease selected from renal fibrosis, particularly when associated with calcification of renal tissue, renal inflammation, particularly when associated with calcification of renal tissue, nephritis, particularly interstitial nephritis, glomerulonephritis, phosphate-induced renal fibrosis, phosphate-induced chronic kidney disease, chronic kidney disease associated with hyperphosphatemia, progression of chronic kidney disease, phosphate toxicity, hyperphosphaturia, hyperphosphatemia, and/or hyper-FGF23-emia, for weekly administration.

The compounds of the invention are similarly provided for use in a method of manufacture of a medicament for the treatment or prevention of a disease associated with formation of calcium salt precipitate or calcium salt crystals, the disease being selected from vascular calcification, coronary artery disease, vascular stiffening, valvular calcification, nephrocalcinosis, calcinosis cutis, kidney stones, and chondrocalcinosis.

Similarly, the invention encompasses methods of treatment of a patient having been diagnosed with a disease associated with formation of calcium salt precipitate or calcium salt crystals, specifically in a disease selected from renal fibrosis, particularly when associated with calcification of renal tissue, renal inflammation, particularly when associated with calcification of renal tissue, nephritis, particularly interstitial nephritis, glomerulonephritis, phosphate-induced renal fibrosis, phosphate-induced chronic kidney disease, chronic kidney disease associated with hyperphosphatemia, progression of chronic kidney disease, phosphate toxicity, hyperphosphaturia, hyperphosphatemia, and/or hyper-FGF23-emia. This method entails administering to the patient an effective amount of an inositol polyphosphate oligo(ethylene glycol) compound, or its pharmaceutically acceptable salt, as specified in detail herein.

Pharmaceutical Compositions and Administration

Another aspect of the invention relates to a pharmaceutical composition comprising a compound of the present invention, or a pharmaceutically acceptable salt thereof, and a pharmaceutically acceptable carrier. In further embodiments, the composition comprises at least two pharmaceutically acceptable carriers, such as those described herein.

In certain embodiments of the invention, the compound of the present invention is typically formulated into pharmaceutical dosage forms to provide an easily controllable dosage of the drug and to give the patient an elegant and easily handleable product.

In certain embodiments, the pharmaceutical composition for use according to the invention is formulated for administration by intradermal or subcutaneous injection.

The dosage regimen for the compounds of the present invention will vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. In certain embodiments, the compounds of the invention may be administered in a single daily dose, or the total daily dosage may be administered in divided doses of two, three, or four times daily.

The pharmaceutical composition for use according to the present invention can be subjected to conventional pharmaceutical operations such as sterilization and/or can contain conventional inert diluents or buffering agents, as well as adjuvants, such as preservatives, stabilizers, surfactants and buffers, etc. They may be produced by standard processes, for instance by conventional mixing, dissolving or lyophilizing processes. Many such procedures and methods for preparing pharmaceutical compositions are known in the art, see for example L. Lachman et al. The Theory and Practice of Industrial Pharmacy, 4th Ed, 2013 (ISBN 8123922892).

The invention further encompasses the following items:

Item 1: An inositol polyphosphate oligo(ethylene glycol) compound, or its pharmaceutically acceptable salt, for use in treatment or prevention of a disease associated with formation of, and/or tissue exposure to, calcium salt crystals, characterized in that the inositol polyphosphate oligo(ethylene glycol) compound is administered at an interval of one week.

Item 2: The inositol polyphosphate oligo(ethylene glycol) compound, or its pharmaceutically acceptable salt, for use according to item 1, wherein the inositol polyphosphate oligo(ethylene glycol) compound is described by a general formula I (I)

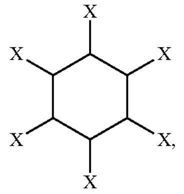

wherein one or two or three X are oligo(ethylene glycol) and the remaining X are $OPO_3^{2-}$.

Item 3: The inositol polyphosphate oligo(ethylene glycol) compound, or its pharmaceutically acceptable salt, for use according to item 2, wherein two X are oligo(ethylene glycol) and the remaining four X are $OPO_3^{2-}$.

Item 4: The inositol polyphosphate oligo(ethylene glycol) compound, or its pharmaceutically acceptable salt, for use according to item 2, wherein three X are oligo(ethylene glycol) and the remaining three X are $OPO_3^{2-}$.

Item 5: The inositol polyphosphate oligo(ethylene glycol) compound, or its pharmaceutically acceptable salt, for use according to item 2, wherein one X is oligo(ethylene glycol) and the remaining five X are $OPO_3^{2-}$.

Item 6: The inositol polyphosphate oligo(ethylene glycol) compound, or its pharmaceutically acceptable salt, for use according to any one of items 2 to Fehler! Verweisquelle konnte nicht gefunden werden., wherein the oligo(ethylene glycol) is described by a formula $O—(CH_2—CH_2—O)_nCH_3$, with n being selected from an integer between 2 and 20, particularly n being 2 to 12.

Item 7: The inositol polyphosphate oligo(ethylene glycol) compound, or its pharmaceutically acceptable salt, for use according to item Fehler! Verweisquelle konnte nicht gefunden werden., wherein n is 2.

Item 8: The inositol polyphosphate oligo(ethylene glycol) compound, or its pharmaceutically acceptable salt, for use according to item 3, wherein the compound is described by any one of the formulas:

1.

(I a)

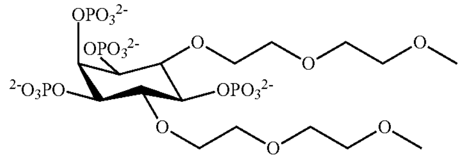

(I b)

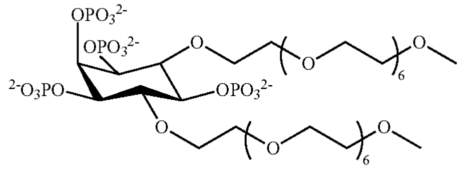

(I c)

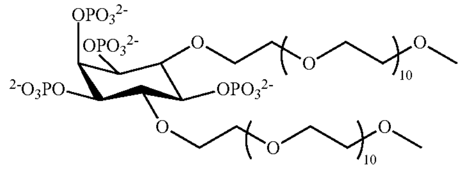

particularly wherein the compound is described by formula Ia.

Item 9: The inositol polyphosphate oligo(ethylene glycol) compound, or its pharmaceutically acceptable salt, for use according to item 5, wherein the compound is described by any one of the formulas:

(I-d)

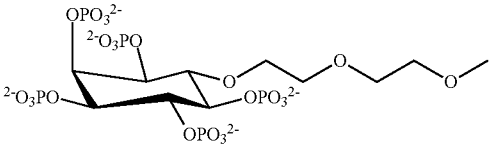

(I-e)

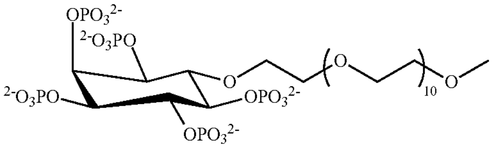

Item 10: The inositol polyphosphate oligo(ethylene glycol) compound, or its pharmaceutically acceptable salt, for use according to any one of the preceding items, wherein the compound is administered to a human patient at a dose of between 60 nmol/kg/day to 2500 nmol/kg/day, particularly at a dose of between 90 nmol/kg/day to 1600 nmol/kg/day, more particularly at a dose of between 170 nmol/kg/day to 600 nmol/kg/day, equivalent to (using the compound (I a) and not calculating the weight of the counterion, MW 698 $gmol^{-1}$) a dose of 40 to 1200 μg/kg/day, particularly at a dose of 65 μg/kg/day to 1100, more particularly at a dose of 120 to 400 μg/kg/day.

Item 11: The inositol polyphosphate oligo(ethylene glycol) compound, or its pharmaceutically acceptable salt, for use according to any one of the preceding items, wherein the compound is administered to a human patient at a dose to sustain a plasma level exceeding 10 ng/mL, particularly at a dose sustaining a plasma level of 10 ng/mL to 50 μg/mL, more particularly at a dose sustaining a plasma level of 100 ng/mL to 5 μg/mL.

Item 12: The inositol polyphosphate oligo(ethylene glycol) compound, or its pharmaceutically acceptable salt, for use according to any one of the preceding items, wherein the compound or its salt are provided for treatment or prophylaxis of a disease selected from:

renal fibrosis, particularly when associated with calcification of renal tissue,
renal inflammation, particularly when associated with calcification of renal tissue,
nephritis,
interstitial nephritis,
glomerulonephritis,
phosphate-induced renal fibrosis,
phosphate-induced chronic kidney disease,
chronic kidney disease associated with hyperphosphatemia,
progression of chronic kidney disease,
phosphate toxicity,
hyperphosphaturia,
vascular calcification,
hyperphosphatemia, and/or
hyper-FGF23-emia.

Item 13: The inositol polyphosphate oligo(ethylene glycol) compound, or its pharmaceutically acceptable salt, for use according to any one of the preceding items, wherein the disease is a disease associated with the formation of calcium phosphate salt or precipitate.

Item 14: The inositol polyphosphate oligo(ethylene glycol) compound, or its pharmaceutically acceptable salt, for use according to any one of the preceding items, wherein the disease associated is a disease associated with the formation of calcium oxalate salt or precipitate, and/or the formation of a mixed calcium phosphate oxalate precipitate.

The invention is further illustrated by the following examples and figures, from which further embodiments and advantages can be drawn. These examples are meant to illustrate the invention but not to limit its scope.

The $Abcc6^{-/-}$ mice receiving (I a) via osmotic pumps at 0.16 mg/kg/day had no effects on calcification in the vibrissae. Osmotic pump delivery of (I a) at 0.8 mg/kg/day had evident but significantly reduced calcification. Subcutaneous injections of (I a) at different doses and injection frequencies all resulted in decreased calcification. (B), Reversal study. All mice were analyzed at 24 weeks of age. von Kossa stains revealed extensive vibrissae calcification in untreated $Abcc6^{-/-}$ mice and (I a) treatment prevented further calcification which was stabilized at time of treatment. Arrows indicate ectopic calcification. Scale bar, 0.4 mm.

Figure 2:
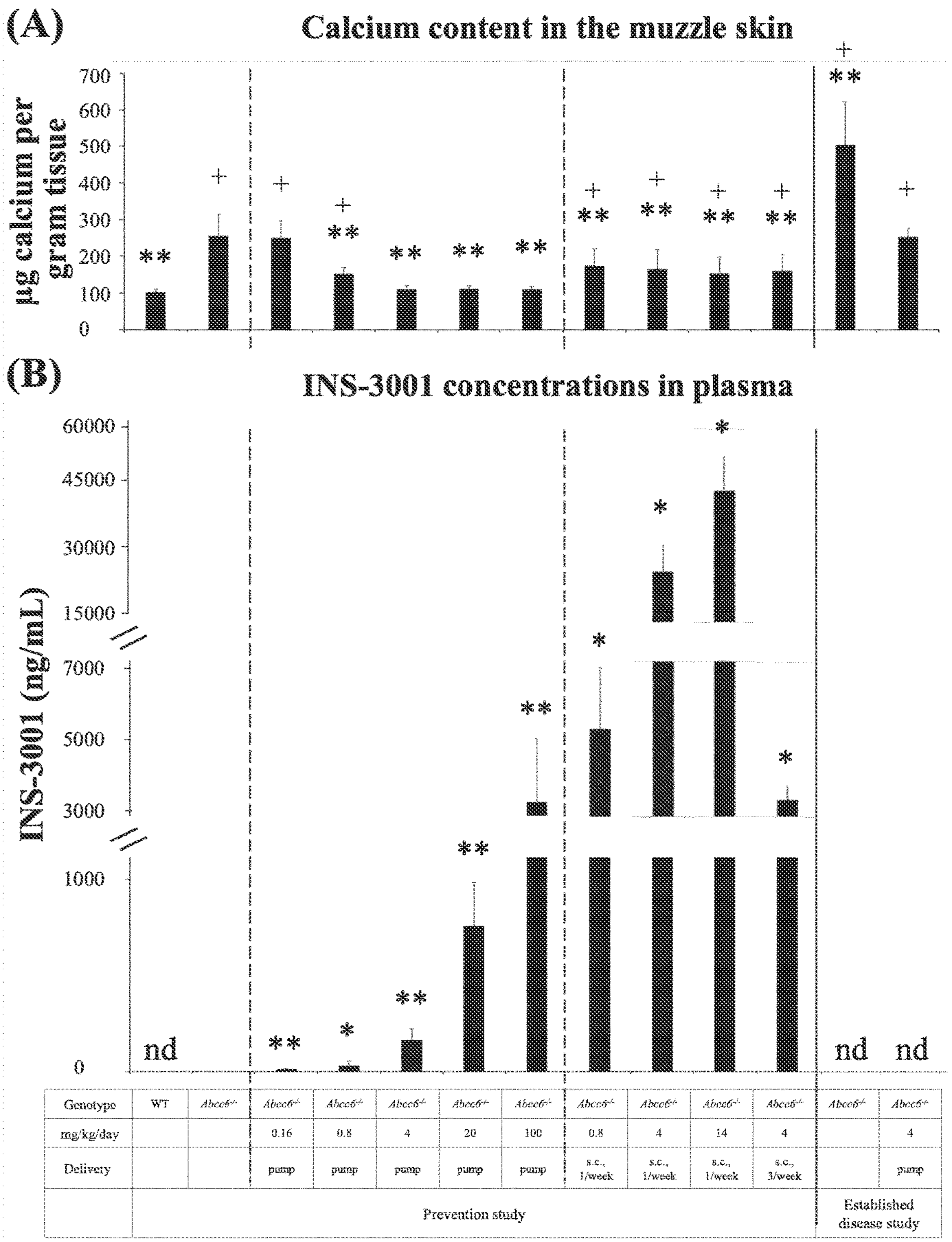

FIG. 2 shows chemical assay of calcium in muzzle skin biopsies and plasma concentrations of INS-3001 in mice receiving (I a) administration. (A), The calcium content in the muzzle skin containing vibrissae. 6-12 mice per group. (B), Plasma concentrations of (I a). 5 mice per group. Blood was collected either prior to sacrifice for mice implanted with osmotic pumps or 30 minutes after a subcutaneous injection. Overall, the plasma concentrations scaled relatively well with the dose administered despite variabilities among different groups. The variability may be due to the fact that a single sampling time point was chosen around the anticipated $T_{max}$ of 30 minutes, which leads to greater variability than if a complete pharmacokinetic profile had been obtained. *P<0.05, **P<0.01, compared to untreated 12-week-old Abcc6 mice; +P<0.01, compared to untreated WT mice. Data were presented as mean±SD. nd, not determined.

Figure 3:
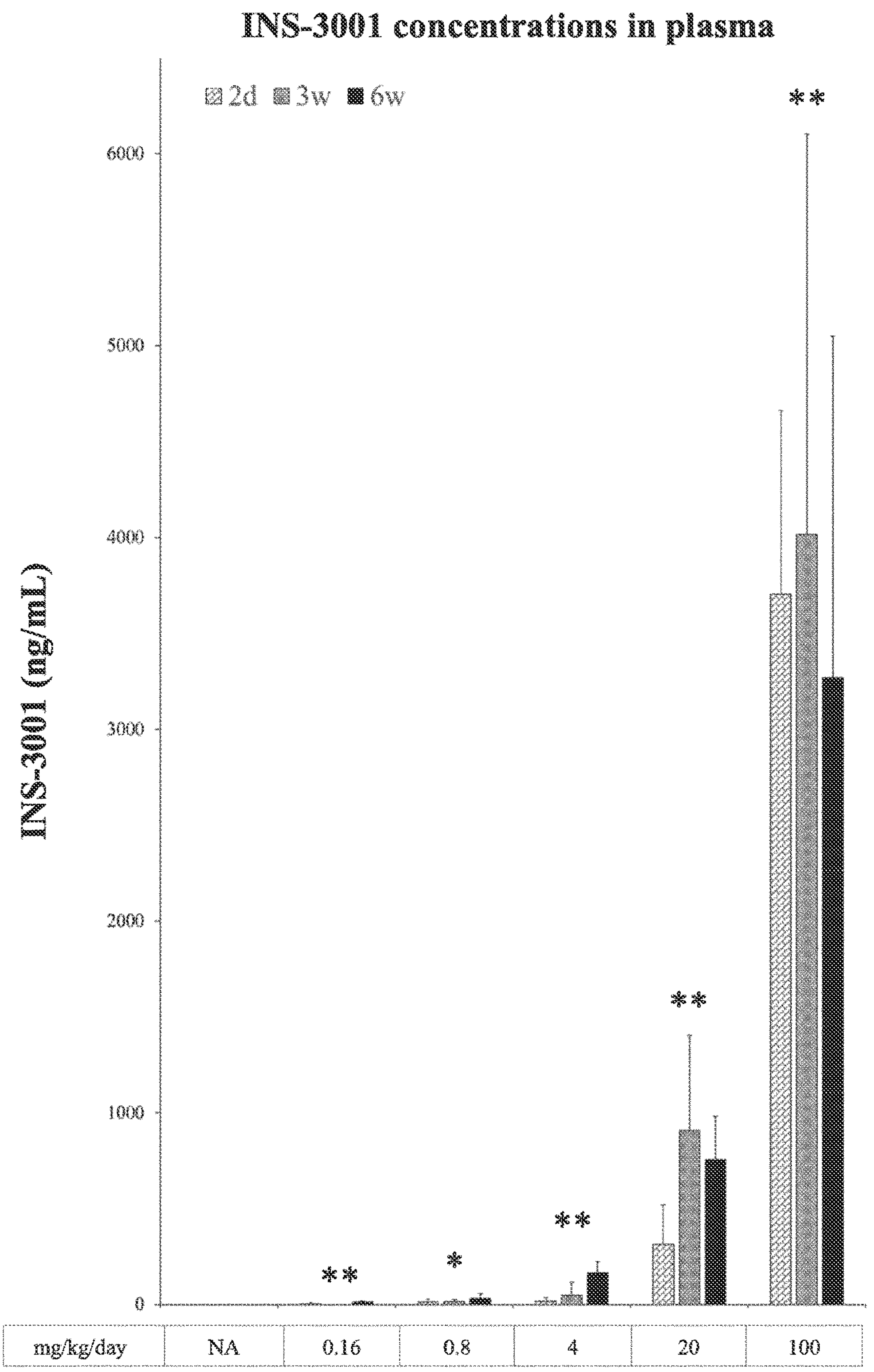

FIG. 3 shows plasma concentrations of (I a) in mice receiving continuous (I a) administration via osmotic pump. Blood was collected at 2 days, 3 weeks, and 6 weeks after subcutaneous implantation of osmotic pumps filled with (I a) solution to deliver (I a) at 0.16, 0.8, 4, 20, and 100 mg/kg/day. 5 mice per group. *P<0.05, **P<0.01, compared to untreated $Abcc6^{-/-}$ mice. Data were presented as mean±SD.

EXAMPLES

Material and Methods $Abcc6^{-/-}$ knock-out mice ($Abcc6^{-/-}$) on C57BL/6J background were generated as described previously (J. F. Klement et al., Mol Cell Biol 2005, 25, 8299). C57BL/6J mice from The Jackson Laboratory (Bar Harbor, ME) were used as wild-type controls (WT). In prevention study, 6-week-old Abcc6$^{-/-}$ mice were administered with (I a) by periodic subcutaneous injections or continuous administration via subcutaneous ALZET osmotic pump model 2006 (DURECT Corp, Cupertino, CA) for duration of 6 weeks. In reversal study, 12-week-old Abcc6$^{-/-}$ mice were administered (I a) at 4 mg/kg/day via osmotic pumps for 12 weeks. All mice were maintained on a standard diet and sacrificed at 12 weeks of age, 6 weeks after initiation of treatment (prevention study), or at 24 weeks of age, 12 weeks after initiation of treatment (reversal study). All protocols were approved by the Institutional Animal Care and Use Committee of Thomas Jefferson University.

Muzzle skin biopsies (left side) from euthanized mice were collected and fixed in 10% phosphate-buffered formalin and embedded in paraffin. Paraffin sections (6 μm) were stained with Hematoxylin and Eosin or von Kossa using standard procedures. To quantify the mineral deposition, muzzle skin biopsies (right side) were harvested and decalcified with 1.0 M HCl for 48 hours at room temperature. Solubilized calcium was then determined by a colorimetric assay (J. Huang et al., J Invest Dermatol 2019, 139, 1254; Q. Li, J. Huang et al., J Invest Dermatol 2019, 139, 360). The values were normalized to tissue weight. Whole blood was collected by retro-orbital bleeding or cardiac puncture. For subcutaneously injected mice, whole blood was collected 30 minutes after injection of (I a). Whole blood was collected at 2 days, 3 weeks, and 6 weeks after treatment initiation in mice receiving (I a). The concentrations of (I a) in heparin plasma were analyzed on an ultra-fast liquid chromatography, as described previously (A. E. Schantl et al., Nat Commun 2020, 11, 721). The data was analyzed using Kruskal-Wallis nonparametric test. Statistical significance was reached with $P<0.05$.

Results

Example 1: Prevention Study: Continuous Delivery of (I a) in Young Abcc6$^{-/-}$ Mice The Abcc6$^{-/-}$ mice were administered (I a) by subcutaneous implantation of osmotic pumps at doses of 0.16, 0.8, 4, 20, and 100 mg/kg/day. The untreated wild-type and Abcc6$^{-/-}$ mice served as negative and positive controls of ectopic calcification. Treatment was initiated at 6 weeks of age, a time point at the earliest stages of ectopic calcification in the Abcc6$^{-/-}$ mice. The extent of ectopic calcification after 6 weeks of treatment was analyzed by two independent assays measuring calcification in the dermal sheath of vibrissae in muzzle skin, an early and reliable biomarker in this mouse model of PXE. One piece of muzzle skin was processed for semi-quantitative histological evaluation. A calcium-specific stain, von Kossa staining, revealed robust calcification in the dermal sheath of vibrissae in the untreated Abcc6$^{-/-}$ mice at 12 weeks of age. The Abcc6$^{-/-}$ mice receiving (I a) at concentrations at and above 4 mg/kg/day showed little, if any, calcification in the muzzle skin. There is no dose correlation with (I a) at the range of 4-100 mg/kg/day, as the lowest dose of 4 mg/kg/day completely prevented ectopic calcification to the same extent as the highest dose of 100 mg/kg/day (almost 100% inhibition). Significantly reduced calcification was noted at 0.8 mg/kg/day, by contrast, 0.16 mg/kg/day showed no effects on prevention of muzzle skin calcification (FIG. 1A). The therapeutic effects of (I a) were substantiated by the calcium content in another muzzle skin biopsy measured using a quantitative chemical assay (FIG. 2A). The results showed that the levels of calcium in the (I a) treated Abcc6$^{-/-}$ mice at 4 mg/kg/day and above were similar to those of WT mice negative of ectopic calcification (FIG. 2A). The partial inhibition of ectopic calcification at 0.8 mg/kg/day was corroborated by calcium assay corresponding to 59% inhibition (FIG. 2A), thus 0.8 mg/kg/day was identified as the minimum active dose.

(I a) was undetectable in plasma of untreated Abcc6$^{-/-}$ mice. Administration of (I a) at doses from 0.16 to 100 mg/kg/day resulted in dose-dependent plasma concentrations (FIG. 2B). In addition, the levels of (I a) remained largely constant at 2 days, 3 weeks, and 6 weeks after implantation of the osmotic pump (FIG. 3), attributed by the nature of the consistent and continuous release of (I a) via osmotic pump.

Example 2: Prevention Study: Intermittent Subcutaneous Injections of (I a) in Young Abcc6$^{-/-}$ Mice (I a), when delivered continuously by osmotic pump at 4 mg/kg/day, completely prevented ectopic calcification in the muzzle skin of Abcc6$^{-/-}$ mice. The inventors next examined whether periodic, bolus subcutaneous injections of (I a) at the same dose of 4 mg/kg/day, would have similar therapeutic benefits. Six-week-old Abcc6$^{-/-}$ mice were administered (I a) by subcutaneous injections three times per week corresponding to 4 mg/kg/day. These mice showed significantly reduced calcification in the muzzle skin 6 weeks after start of treatment but residual calcification was still evident (FIG. 1A), corresponding to 63% inhibition (FIG. 2A). Thus, subcutaneous injection of (I a) is effective, albeit less than with continuous delivery at the same dose of 4 mg/kg/day on inhibition of ectopic calcification.

Three additional dose levels of (I a) at weekly subcutaneous injections for a duration of 6 weeks were tested to evaluate the inhibitory effects of (I a) (FIG. 1A). The efficacy of weekly injection at 14 mg/kg/day was similar to 4 mg/kg/day three injections per week, suggesting that transient increase of plasma levels of (I a) might be beneficial. The Abcc6$^{-/-}$ mice receiving (I a) injection at weekly frequency of 4 mg/kg/day showed significantly reduced calcification, similar to the effects with the same dose but at frequency of three injections per week. Weekly injection of (I a), at dose as low as 0.8 mg/kg/day, also significantly reduced ectopic calcification, suggesting that (I a) is a potent inhibitor of ectopic calcification with pharmacological activity that is maintained over days. The semi-quantitative histologic evaluations of (I a) treatment were consistent with the calcium contents in the muzzle skin measured by a chemical assay (FIG. 2A).

The $T_{max}$ of (I a) in plasma after subcutaneous administration in Sprague Dawley rats was reported to be about 30 minutes after injection, the inventors therefore measured (I a) concentrations in plasma 30 minutes after injection in the Abcc6$^{-/-}$ mice. (I a) levels in plasma 30 minutes after injection were much higher than that in the pump administered groups, as expected for a bolus administration (FIG. 2B). (I a)-mediated prevention of ectopic calcification was more effective with continuous delivery reaching steady-state plasma concentrations, whereas bolus injections resulted in transient increase of (I a) concentrations but was still significantly potent when administered periodically.

Figure 1:
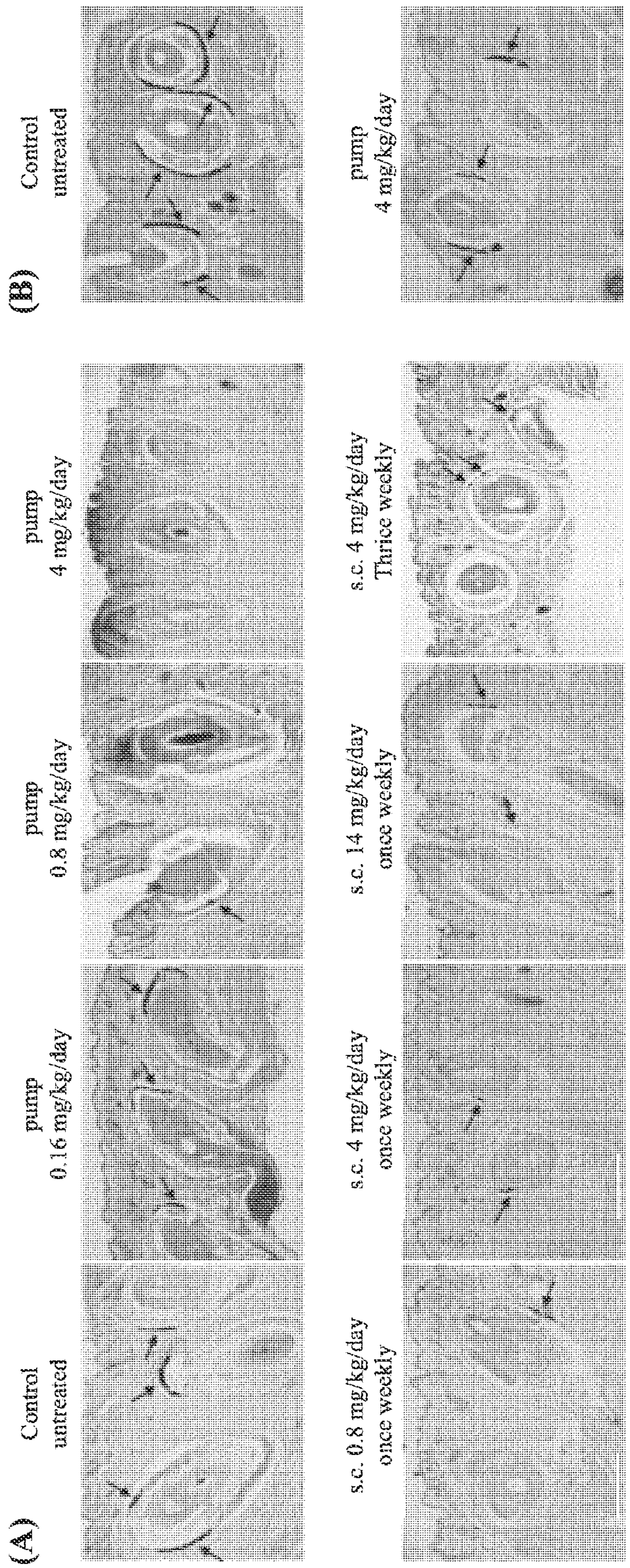
FIG. 1 shows histopathologic examination of vibrissae calcification in the muzzle skin of $Abcc6^{-/-}$ mice in different groups. (A), Prevention study. All mice were analyzed at 12 weeks of age. von Kossa stains revealed robust calcification in the dermal sheath of vibrissae in untreated $Abcc6^{-/-}$ mice. The $Abcc6^{-/-}$ mice receiving (I a) via osmotic pumps at 4 mg/kg/day had very little, if any, calcification in the vibrissae.

Example 3: Treatment Study: Continuous Delivery of (I a) in Old Abcc6$^{-/-}$ Mice In the treatment study Abcc6$^{-/-}$ mice were aged to 12 weeks, the time at which ectopic calcification was extensive in the muzzle skin containing vibrissae (FIG. 1B). (I a) was administered at 4 mg/kg/day by osmotic pump, a dose and delivery route that resulted in a complete response in the young mice (FIG. 1A). The degree of ectopic calcification was evaluated 12 weeks later. Histopathology and calcium assay of the muzzle skin in the (I a) treated mice demonstrated calcification similar to 12-week-old Abcc6$^{-/-}$ control mice (FIG. 1, 2A). These results demonstrated that (I a), for a total of 12 weeks of follow-up, stabilized existing calcification and stopped the further growth of calcifications.

CONCLUSION

The inventors' results demonstrated that (I a) treatment prevented muzzle skin calcification in the Abcc6$^{-/-}$ mice with concurrent increases in its plasma levels, suggesting that pharmacologic therapy with (I a) might provide a promising treatment strategy for spontaneous calcification in PXE and GACI type 2, diseases that currently lack preventive or therapeutic options. The mechanism of action of (I a) as a new calcification inhibitor are not through chelation of calcium but rather coating of calcifications to hinder apposition of further mineralization. This mode of action is similar to that of the natural compound IP6, which was recently reported to stop the progression, albeit without regression, of cardiovascular calcifications in patients on hemodialysis following a 1-year treatment. (I a) arrested further deposition of mineral at the point when the treatment was initiated, suggesting that if (I a) is to be used to treat patients with PXE, it should be started as soon as the diagnosis is made. In contrast to chaperone-based allele-specific therapies, (I a) might have the potential to treat PXE regardless of the types of mutations in ABCC6. Compared to pyrophosphate and bisphosphonates, (I a) has high subcutaneous bioavailability, good local tolerability, high potency and no anti-osteoclastic activity.

The invention claimed is:

1. A method for treatment of a disease associated with formation of, and/or tissue exposure to, calcium salt crystals, comprising administering to a subject in need thereof an inositol polyphosphate oligo (ethylene glycol) compound described by a compound selected from any one of the formulas Ia, Ib, or Ic:

(I a)

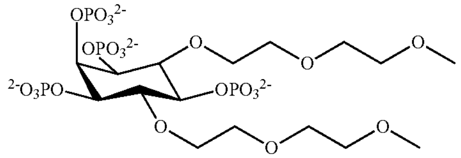

-continued (I b)

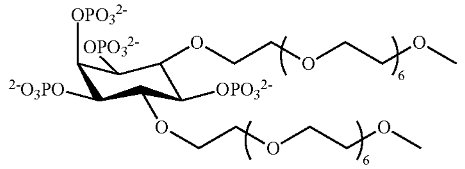

(I c)

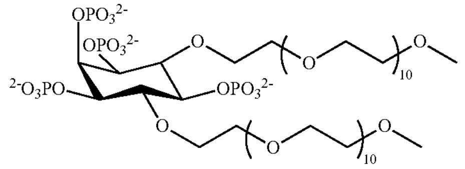

or the pharmaceutically acceptable salt of said compound wherein the inositol polyphosphate oligo (ethylene glycol) compound is administered to the subject at an interval of one week.

2. The method according to claim 1, wherein the compound is described by formula Ia.

3. The method according to claim 1, wherein the disease associated with formation of, and/or tissue exposure to, calcium salt crystals is valvular calcification.

4. The method according to claim 1, wherein the disease associated with formation of, and/or tissue exposure to, calcium salt crystals is a disease selected from:

renal fibrosis,
renal inflammation,
nephritis,
interstitial nephritis,
glomerulonephritis,
phosphate-induced renal fibrosis,
phosphate-induced chronic kidney disease,
chronic kidney disease associated with hyperphosphatemia,
progression of chronic kidney disease,
phosphate toxicity,
hyperphosphaturia,
hyperphosphatemia, and/or
hyper-FGF23-emia.

5. The method according to claim 1, wherein the disease is a disease associated with the formation of calcium phosphate salt or precipitate.

6. The method according to claim 1, wherein the disease is a disease associated with the formation of calcium oxalate salt or precipitate, and/or the formation of a mixed calcium phosphate oxalate precipitate.

7. The method according to claim 4, wherein the renal fibrosis is associated with calcification of renal tissue.

8. The method according to claim 4, wherein the renal inflammation is associated with calcification of renal tissue.

* * * * *